United States Patent
Hart

(10) Patent No.: US 6,732,054 B2
(45) Date of Patent: May 4, 2004

(54) PROCESS FOR IDENTIFYING SINGLE CRYSTALS BY ELECTRON DIFFRACTION

(75) Inventor: Haskell Vincent Hart, Katy, TX (US)

(73) Assignee: Shell Oil Company, Houston, TX (US)

( * ) Notice: Subject to any disclaimer, the term of this patent is extended or adjusted under 35 U.S.C. 154(b) by 53 days.

(21) Appl. No.: 10/301,326

(22) Filed: Nov. 21, 2002

(65) Prior Publication Data

US 2003/0168593 A1 Sep. 11, 2003

Related U.S. Application Data

(60) Provisional application No. 60/333,583, filed on Nov. 27, 2001.

(51) Int. Cl.$^7$ ................................................ H01J 37/28
(52) U.S. Cl. ............................ 702/28; 250/305; 378/73
(58) Field of Search ........................... 702/28; 250/305, 250/307, 310, 311; 378/73, 86

(56) References Cited

U.S. PATENT DOCUMENTS

| | | | |
|---|---|---|---|
| 4,553,030 A | 11/1985 | Tokiwai et al. | 250/307 |
| 5,168,457 A | 12/1992 | Karen et al. | 364/497 |
| 5,235,523 A | 8/1993 | Karen et al. | 364/497 |

FOREIGN PATENT DOCUMENTS

| | | | |
|---|---|---|---|
| JP | 7282769 | 10/1995 | H01J/37/295 |

OTHER PUBLICATIONS

Mighell, A.D., etc., "D–spacing/Formula Index for Compound Identification using Electron Diffraction Data" *Proceedings of the 46$^{th}$ Annual Meeting of the Electron Microscopy Society of America*, 912–913.

Griem, W., etc., Computer Assisted Indexing of Electron Diffraction Patterns. *Praktische Metallographic*, 14, 1977, 389–409.

Wilkes, P., etc., "Complete Indexing of Electron Diffraction Patterns by Computer" *Journal of Materials Science*, 9, 1974, 517–518.

Booth, M., etc., "A General Program for Interpreting Electron Diffraction Data" *Metallurgical Transactions*, vol. 5, Mar. 1974, 775–776.

Goehner, R.P., etc., "Computer–Aided Indexing of Transmission Electron Diffraction Patterns" *Metallography*, 10, 1977, 415–424.

Mighell, A., etc., "NIST Crystallographic Databases for Research and Analysis" *Journal of Research of the National Institute of Standards and Technology*, vol. 101, No. 3, 273–280.

Anderson, R., etc., "Electron Diffraction Database", *Microscopy Society of America Bulletin*, vol. 23, No. 1, 128–137.

Lally, J.S., etc., "Computer Indexing of Electron Diffraction Patterns Including the Effect of Lattice Symmetry" *Electron Microsc, X–ray Appl. Environ. Occup. Health Anal.*, Second Symposiu, Ann Arbor Society, An Arbor Michigan, 1978, 169–174.

Carr, M., etc., "A Search/Match Procedure for Electron Diffraction Data Based on Pattern Matching in Binary Bt Maps", *Powder Diffraction*, vol. 1, No. 3, 226–234.

*Primary Examiner*—Kamini Shah
(74) *Attorney, Agent, or Firm*—Y. Grace Tsang

(57) ABSTRACT

A relational database is built and used for the identification of single crystals by electron diffraction. Selected area electron diffraction (SAED) patterns (a lattice net of spots) produced in an electron diffractometer or a transmission electron microscope (TEM) are matched against database patterns calculated from reduced unit cells of known materials. The effects of double diffraction on electron diffraction patterns are fully incorporated into the database by rigorous calculation.

6 Claims, No Drawings

PROCESS FOR IDENTIFYING SINGLE CRYSTALS BY ELECTRON DIFFRACTION

This application claims the benefit of U.S. Provisional Application Ser. No. 60/333,583 filed Nov. 27, 2001, the entire disclosure of which is hereby incorporated by reference.

BACKGROUND OF THE INVENTION

Electron diffraction is an identification technique for solid crystalline phases, particles, and surfaces observed in a transmission electron microscope (TEM) or other electron diffractometer. It is often used in conjunction with elemental analysis, which is often performed by fluorescence spectrometry (called EDS for energy dispersive spectrometry) on the TEM. Together these techniques are used by scientists to identify the chemical composition and structure of unknown materials of very small size, typically 10's to 1000's of nanometers (nm), in the fields of metallurgy, catalysis, analytical chemistry, mineralogy, forensics, and environmental studies.

Identification of a known single crystal phase by electron diffraction takes the form of interpreting a lattice net of spots produced in the diffraction mode of the TEM or electron diffractometer. Images can be recorded by (a) a fluorescent screen and photographic film, or (b) an electronic detector capable of converting diffracted electron impulses in two dimensional space to electronic signals which are converted, with their spacial positions, to digital form and stored in a computer file.

In case (a) the two minimum repeat distances ($r_1$, $r_2$) of the lattice net and their included acute angle ($\phi$) are measured on the film. The corresponding maximum d-spacings, ($d_1$, $d_2$), in Angstrom units (Å) are calculated from each minimum repeat distance and the electron voltage or electron wavelength and the camera length (the distance between sample and recorder) of the diffractometer or TEM by Equation 1 (see below), or in case (b) the electronic file of converted signal impulses and positions ($r_1$, $r_2$), together with the electron voltage or electron wavelength and the camera length of the diffractometer or TEM is processed through computer programs or other calculations to produce the corresponding maximum d-spacings, ($d_1$, $d_2$), in Angstrom units by Equation 1 shown below:

$$r*d=C*\lambda \quad \text{(Equation 1)}$$

wherein
- r=distance of spot from center in centimeters (also known as r-spacing),
- d=d-spacing in Angstroms (1 Å=$10^{-10}$ meter)
- C=camera constant in millimeter-Angstroms,
- $\lambda$=electron wavelength in nanometers, which is determined from the electron voltage by conventional means, using the well known de Broglie Principle and related formulae.

Equation 1 is the well known application of Bragg's Law to electron diffraction (Reference 1). The two r-spacings ($r_1$, $r_2$) are the shortest and second shortest distances, respectively, to the center of the pattern (the direct beam), whereas the two d-spacings ($d_1$, $d_2$) are the largest and second largest d-spacings, respectively, of the zone of the pattern. The included angle, $\phi$, is both the acute angle between the lattice rows containing $r_1$ and $r_2$, respectively, and the interplanar angle (acute) between the sets of parallel planes whose interplanar spacings are, respectively, $d_1$ and $d_2$. These relationships as well as the terms, "d-spacing," "zone," "interplanar," are well known to those skilled in the art of crystallography.

An identification of a previously known material (or phase) is obtained when the values $d_1$, $d_2$, and $\phi$ are matched to measured or calculated values for a known material (References 2, 3).

The values of $d_1$, $d_2$, of known materials are calculated from their unit cells through the well known formula for triclinic unit cells (Reference 4) by varying Miller Indeces (h,k,l) from among those found in FIG. 1. These combinations ($h_1$, $k_1$, $l_1$) and density (and low zone indeces [U,V,W] (FIG. 1.). These zones will also exhibit the highest spot symmetry in their electron diffraction patterns and will therefore be recognizable as the most desirable zones to be measured experimentally. The angle $\phi$ is calculated from the well known formula for tricilinic unit cells (Reference 4).

Candidate materials for a "hit" are found by matching the values of $d_1$, $d_2$, and $\phi$ determined experimentally to the values calculated from the unit cells of the known materials. Often the solutions above are not unique. In such cases, elemental analysis, for example by fluorescence spectrometry mentioned above, usually decides in favor of one or a very few possible, often chemically or structurally related, phases. Knowledge of sample history or other physical or analytical data might also be required for the final identification.

Prior art of comprehensive databases for electron diffraction is described in References 5, 6, 7, 8, and 9 and is summarized below.

The Powder Diffraction File, or PDF (Reference 6) of the International Centre for Diffraction Data (ICDD) is an x-ray polycrystalline diffraction database of d-spacings and other crystallographic data which is available in computer, microfiche, or book form. Its known disadvantage for use in electron diffraction is that it does not include d-spacings observed by double diffraction, because double diffraction is rare in x-ray diffraction.

Double diffraction is the phenomenon of a diffracted beam being rediffracted before exiting the crystal. The effect of this important phenomenon is that d-spacings which are unobservable ("extinct") by x-radiation appear in the electron diffraction pattern of the same material, as if there were no three-dimensional symmetry elements. These additional d-spacings due to double diffraction, which fill in x-ray extinct values, are included automatically if one calculates electron diffraction patterns from a reduced unit cell. This is the premise of ZONES. In this manner, no extra rings are calculated and none are missed. Further, there are no symmetry considerations.

Even more importantly, the PDF contains no interplanar angles ($\phi$). One might use two d-values as $d_1$ and $d_2$ and calculate the interplanar angle from the Miller indeces (h,k,l) of each, which are usually on the PDF card for each material. This is a slow procedure of limited applicability to single crystal identifications which have very limited possible solutions.

The NIST/ICDD/Sandia Electron Diffraction Database (References 5, 6) is a polycrystalline computer database developed specifically for electron diffraction, incorporating both the PDF and NIST Crystal Data (described below). Since it contains no interplanar angles, it would have to be used for $d_1$ and $d_2$ only, requiring a separate calculation of $\phi$. Since no Miller indeces are included in this database, it would be even more cumbersome to use than the PDF for single crystal electron diffraction.

Another database is available in book form only, the Elemental and Interplanar Spacing Index (EISI), available from ICCD. (References 6, 7) On one line per phase it contains an alphabetical listing of elements (by symbol) and the highest ten d-spacings in decreasing order. However it is a polycrystalline database as are the above databases, and therefore the EISI does not include interplanar angles ($\phi$). Nor does it include the effects of double diffraction. Its use for polycrystalline electron diffraction is discussed in Reference 6. For single crystal electron diffraction it has the same shortcomings as as the preceding databases with respect to interplanar angles.

NIST Crystal Data, currently in Release J of 1997 on CD-ROM, began in the mid-1980's as a large computer file (first available on tape) of crystallographic and related data obtained from several other original sources: ICDD (then known as The Joint Committee for Powder Diffraction Standards—JCPDS), The Cambridge Crystallographic Centre (U.K.), The Metals Data Center (Ottawa, Canada), The Inorganic Structural Data Center (Germany), and the open literature. Today, the database contains information on 237,659 organic, inorganic, and organometallic phases (of which 79,136 are inorganic) and is available on CD-ROM from NIST or ICDD (References 5, 6, 8). For each phase (also called a "known material", as defined above), the data is organized into sixteen different types of several related fields each (Reference 8). The CD-ROM contains a single flat text file of these types for each phase, plus a coded literature reference file (one of the fields), and various special use files, not used here. There are no d-spacings or any PC software for searching or organizing the data in Release J, 1997, on CD-ROM. However, through its reduced unit cells, this database forms the basis for calculating diffraction patterns in the ZONES database.

In addition, an electron microscopist trained in crystallography might, in favorable circumstances, obtain two zone axis patterns and the interaxial angle between them. NIST has written software to compute the reduced unit cell from this data, which can be searched against the NIST Crystal Data reduced unit cell fields (References 5, 6, 8). This is a powerful and patented (Reference 9) search/match procedure in the hands of a specialist, but it is not as simple as matching three numbers ($d_1$, $d_2$, $\phi$). There is considerable mathematical complexity in determining reduced unit cell parameters from diffraction data by procedures guaranteed to produce the same ("unique", "conventional") result (from among all the possible permutations) of a, b, c, and of $\alpha$, $\beta$, $\gamma$, regardless of which two crystal zone axis patterns are used. It can also be difficult to obtain the required two zone axis patterns and their interaxial angle from the same crystal.

SUMMARY OF THE INVENTION

The present invention is directed to a method for creating a searchable database of crystal electron diffraction data comprising: (a) creating tables within a relational database, said tables comprising Code data, Formula data, and Element data; wherein said Code data includes information relating to the d-spacings and acute angles of diffraction patterns of crystals, said Formula data includes information relating to the chemical formulae of said crystals, and said Element data includes information relating to the presence of elements of high atomic number in said crystals; (b) creating at least one macro for performing searches using said tables; said at least one macro including the steps of: (i) requesting input data relating to observed d-spacings, acute angles, experimental error limits, and anticipated atomic numbers of an experimental sample; (ii) comparing said input data with the data in said tables in accordance with said experimental error limits; and (iii) generating at least one report listing the crystals within said tables that match said input data.

The invention is also directed to a method for classifying crystal electron diffraction data obtained from an experimental sample, comprising: (a) generating a relational database comprising: (i) at least three tables holding Code data, Formula. data, and Element data, respectively; wherein said Code data includes information relating to the d-spacings and acute angles of diffraction patterns of crystals, said Formula data includes information relating to the chemical formulae of said crystals, and said Element data includes information relating to the presence of elements of high atomic number in said crystals; (ii) at least one macro for performing searches using said tables; said at least one macro including the steps of: (1) requesting input data relating to observed d-spacings, acute angles, experimental error limits, and anticipated atomic numbers of an experimental sample; (2) comparing said input data with the data in said tables in accordance with said experimental error limits; and (3) generating at least one report listing the crystals within said tables that match said input data; and (b) using said macro of said relational database to enter electron diffraction data obtained from said experimental sample and to obtain said at least one report.

The invention also provides a relational database for classifying crystal electron diffraction data obtained from an experimental sample, said database comprising: (a) at least three tables holding Code data, Formula data, and Element data, respectively; wherein said Code data includes information relating to the d-spacings and acute angles of diffraction patterns of crystals, said Formula data includes information relating to the chemical formulae of said crystals, and said Element data includes information relating to the presence of elements of high atomic number in said crystals; (b) at least one macro for performing searches using said tables; said at least one macro including the steps of: (i) requesting input data relating to observed d-spacings, acute angles, experimental error limits, and anticipated atomic numbers of an experimental sample.; (ii) comparing said input data with the data in said tables in accordance with said experimental error limits; and (iii) generating at least one report listing the crystals within said tables that match said input data.

DETAILED DESCRIPTION OF THE INVENTION

The present invention provides the construction and searching of a relational database of values $d_1$, $d_2$, and $\phi$, plus coded elemental composition, for known crystalline solids. Through the use of new software and computational methods and procedures associated with this relational database, unknown materials are matched to 79,136 inorganic compounds in embodiment.

The present invention provides the following advantages: (1) it permits an electron microscopist with little or no training in crystallography, and (2) only elementary training in common personal computer (PC) software tools to (3) identify the substance or substances which produced a single crystal electron diffraction pattern from (4) among as wide as possible a set of "knowns". In the present invention, identification of all inorganic materials in the NIST Crystal Data file, in (5) less than 14 seconds search time (the common limit of human patience in such matters)is accomplished.

All of the above five advantages are met with the present invention. Unique features of this invention not found elsewhere are: (1) Rational inclusion in the database of specific d-spacings which produce spots by "double diffraction"

through the use of reduced unit cell parameters; (2) use of a commercially available database management system, in this embodiment, Microsoft ACCESS 97, for producing the relevant crystallographic and elemental parameters and storing these and other phase data in a relational database with database "objects" such as "tables," "queries," "macros," "reports," and "modules" (Visual Basic for Applications code in this embodiment). (3) Use of experimental error limits for $d_1$, $d_2$, and $\phi$ to greatly reduce the number of potential solutions to examine manually in the table, (4) below, and (4) production of an output table and report which can be further customized, sorted, filtered, exported (in common formats), or further reported with common database tools, and (5) ability to customize the search to include other specific information particular to each search problem with common database tools, for example, in this embodiment Microsoft ACCESS 97.

The practice of the invention is accomplished as follows:

1. (a) The values of $d_1$, $d_2$, and $\phi$, along with (b) their error limits as a constant percentage of each d-spacing ($d_1$, $d_2$) and in degrees for $\phi$, and, (c) the element symbols (above atomic number 10 only) for the elements present in the sample (a maximumm of ten), are input to a computer program, ZONES, incorporating a relational database of "known materials," described herein below. A known material in the present embodiment of this invention described here is an inorganic phase present the National Institute of Standards and Technology Crystal Data file, Version J, 1997, (hereinafter referred to as NIST Crystal Data, or NIST CD, or CD—see References 2, 3, 4).

2. The computer program ZONES produces an output table of "candidate materials," defined as "known materials" which match the input requirements of 1.(a) through 1.(c), above. The output table consists of, in one line (or record) per candidate material:

(i) a unique index code (hereinafter called the "CODE") with which other information, not in the output, may be obtained from another database or other source,
  (ii) a chemical formula (hereinafter called "FORMULA"),
  (iii) a matching database value of $d_1$ in Angstroms,
  (iv) a matching database value of $d_2$ in Angstroms,
  (v) a matching database value of $\phi$ in degrees, 3. The "computer program incorporating a relational database of known materials" in 1., above, consists of a collection of relational database "objects," which are: (a) program "modules," in this embodiment written in Microsoft Visual Basic for Applications (VBA) computer program code, and, (b) "tables" and, (c) "queries" of the tables and other tables produced by the queries, (d) "macros" (combinations of database commands, involving tables, queries, modules, and other macros) and, (e) "reports, where "objects," "modules," "tables," "queries," "macros," and "reports" all have the common meanings usually associated with a "relational database," which is in this embodiment of the invention Microsoft ACCESS 97.

4. The CODE in 2. (i) is an index used to retrieve other information on candidate materials, for example through additional relational database tables, queries, macros, and reports.

5. The present embodiment of the "database of known materials" in 1., above, contains: (a) the following tables, wherein each table contains one or more records for each "known material," with a "record" being one line of the table (the usual definition associated with a relational database table):

(i) Database Table tblIZones2. CODE, and $100*d_1$ in Angstroms, as an integer, hereinafter referred to as "100D1; " $100*d_2$, in Angstroms, as an integer, hereinafter referred to as "100D2;" and $10*\phi$, in degrees, as an integer, hereinafter referred to as "10PHI,"
  (ii) Database Table tblIFormulas. CODE and FORMULA,
  (iii) Database Table tblIElements. CODE, N(1), N(2), N(3), N(4), N(5), N(6), N(7) where N(1) to N(7) are the sums of numeric element identifiers for elements with atomic numbers 1–15, 16–30, 31–45, 46–60, 61–75, 76–90, 91–105, respectively, and each numeric element identifier is 2 raised to the power: Z–15* (i–1), where, i is the index of the sums of numeric element identifiers, N(i), ranging from i=1 to i=7 (above), and Z is the atomic number of each element present, and (b) a macro, macZones, which controls the entire search/match procedure, from input to output, and which contains the following separate steps:

(i) Open Module modInputE2
  (ii) Run Code E2( )
  (iii) Close Module modInputE2
    Element symbols are input
    Values of N(i) are calculated according to 5.a (iii).
  (iv) Open Query qryELE2
  (v) Close Query qryELE2
    Table tblIElements is queried for matching values of N(1)–N(7).
    A table, tblELE, of CODE and matching N(1)–N(7) values is produced.
  (vi) Open Module modERRORS
  (vii) Run Code ERRDFile ( )
    % errors in ($d_1$ and $d_2$), are input and written to a file.
    (viii) Run Code ERRPHIFile ( )
    Error in $\phi$ (in degrees) is input and written to a file.
  (ix) Close Module modERRORS
  (x) Open Query qryZones2
  (xi) Close Query qryZones2
    Tables tblELE, tblIZones2, and tblIFormulas are queried for materials with matching elements, and values of $d_1$, $d_2$, and $\phi$ within input error limits.
    An output table of candidate materials, tblZones2, is produced, consisting of CODE, FORMULA, $d_1$, $d_2$, $\phi$, for each.
  (xii) Open Report rptzones
    A Report is produced from Table tblZones2.
  (xiii) Delete tblELE
    Table tblELE is deleted in preparation for the next search.

The 25 zones (per each CODE or known material) of FIG. 1 are reduced in number by symmetry, with redundant combinations of $d_1$, $d_2$, $\phi$, removed before storing the results in a data file as integers 100D1, 100D2, 10PHI in 5. (a) (i), above. This process is repeated for each known material with a reduced unit cell. The resulting datafile of ≦25 unique combinations of 100D1, 100D2, 10PHI, and associated CODE for each known material, is read into the database as Table tblIZones2.

The database table tblIFormulas in 5. (a) (ii) is produced by reading an external datafile containing records of CODE and FORMULA for each known material into the table.

The database table tblIElements in 5. (a) (iii) is produced by reading a datafile of CODE, N(1), N(2), N(3), N(4), N(5), N(6), N(7) for each known material into the database table. This datafile is produced from the external file in 6. by searching each FORMULA for each of the 105 chemical symbols, assigning appropriate numeric indicators for each element symbol found according to 5. (a) (iii), and totaling these numeric indicators within each atomic number range (1 through 7) as in 5. (a) (iii).

The CODE for each known material is consistent throughout the relational database, so that it is possible to relate it to the elements present, the FORMULA, and all stored values of 100D1, 100D2, and 10PHI in a unique manner. Similarly, in the macro macZones, the CODE for each known material is used consistently throughout all queries, intermediate tables, macros, modules, and reports.

Running a Search/Match

The steps required to run a search/match of a single crystal electron diffraction pattern in ZONES, using the present embodiment of this invention, are:

(1) Open the macro macZones.

(2) In Input box 1: From the keyboard, enter a symbol of an element known to be present (Z>10). Repeat for each element (Z>10) known to be present. No unspecified heavy elements will be allowed in the solution, and all specified elements must be present. This requires a complete x-ray fluorescence (or other comparable elemental) analysis. Enter "0" (zero) to stop adding elements. All elements with $Z \leq 10$ cannot be entered and are considered to be possibly present (i.e., any combination of these light elements, including none, is allowed).

(3) Input box 2a: Enter $d_1$, the largest d-value of the zone, in Angstroms.

(4) Input box 2b: Enter $d_2$, the second largest d-value of the zone, in Angstroms.

(5) Input box 2c: Enter $\phi$, the angle between the repeat distances in the diffraction pattern corresponding to $d_1$ and $d_2$, respectively, in degrees.

(6) Input box 3a: Enter the experimental error limit on d-values in % (recommended input 1.5). A match occurs when a database d-value is within this percent of the experimental value, i.e. when $$(100-err.\ d)*d(exptl.) \leq [100D(database,\ 1\ or\ 2)] \leq (100+err.\ d)*d(exptl.).$$

(7) Input box 3b: Enter the experimental error limit on $\phi$ in degrees (recommended input 1.0). A match occurs when $$10*(\phi(exptl.)-err.\ \phi) \leq [10PHI(database)] \leq 10*(\phi(exptl.)+err.\ \phi).$$

BRIEF DESCRIPTION OF THE TABLES

Table 1. Stored Zones.
Table 2. Fluorite.
Table 3. Zircon.
Table 4. Molybdite.
Table 5. Hornblende, first zone.
Table 6. Hornblende, second zone.
Table 7. $Fe_3C$.
Table 8. Hollandite, first zone.
Table 9. Hollandite, second zone.
Table 10. $M_2X$, first zone, Nb.
Table 11. $M_2X$, second zone, Nb.
Table 12. $M_2X$, first zone, Ni.
Table 13. $M_2X$, second zone, Ni.
Table 14. $M_6C$, Cr, Nb.
Table 15. $M_6C$, Fe, Nb.
Table 16. $ZrH_2$.
Table 17. Search Simulations.

EXAMPLES

In the following examples all searches were of the entire database of 79,136 phase entries. No other information about the sample was used, such as mineral, alloy, etc.

Example 1

Table 2 shows output for real input data from fluorite, $CaF_2$, as measured on film: $d_1$=3.19 A, $d_2$=3.18 A, $\phi$=70.2 deg. All phases are correct except one (Ca), which has the poorest d-matches.

Example 2

Table 3 shows output for a search with uncalibrated film data from zircon, $ZrSiO_4$, $d_1$=4.51 A, $d_2$=2.69 A, $\phi$=78.6 deg. Three zircon phases are found.

Example 3

Molybdite, $MoO_3$, is a TEM standard used to calibrate the rotational effect in going from transmission mode to diffraction mode. A common diffraction pattern has $d_1$=3.96 A, $d_2$=3.70 A, $\phi$=90.0 deg. Table 4 gives the results of such a search, with six $MoO_3$ phases found. These reflections are produced by double diffraction and are absent in the Powder Diffraction File (see below) for $MoO_3$.

Example 4

Table 5 shows output for literature experimental data on hornblende, $Ca_2(Mg,\ Fe)Si_8O_{22}(OH,\ F)_2$ (Reference 10). The pattern was successfully identified with ZONES, without the need to index. Table 6 shows results from a second zone of hornblende (assumed) from another reference (Reference 11) by the same author. Both literature references assume hornblende to index the reflections, but we assumed only its elemental information (Ca, Fe, Mg, Si) and searched for the structure as an unknown.

Example 5

Table 7 shows output for $Fe_3C$ from (Reference 12) considered as unknown data for a phase containing Fe. The experimental data had large errors of 4% and 2 deg., yet the correct phase solution was uniquely obtained, plus one boron isomorph. The reference assumed the known structure to index the reflections.

Example 6

Tables 8 and 9 are output for two zones from hollandite, $BaMn_8O_{16}$ (Reference 13.). This example illustrates the case of obtaining two different zone axis patterns from the same physical crystal or chemically identical crystals in different orientations. Obviously, the same phase should be obtained as the solution for each, which is the case here. The authors used their own Minerals Database of 3822 minerals. Our search was over the entire NIST CD-derived inorganic database of 79,136 phases.

Example 7

Example 7 (Tables 10–15) is multifaceted (Reference 14). In this article the authors index forty zone axis electron diffraction patterns from various grains of Inconel 625 alloy containing the following major elements: Cr, Ni, Fe, Mo, Nb, plus others: C, Si, Mn, P, S, Ti, Al, N. They assumed six unit cells corresponding to the following possible phases (M=metal, X=nonmetal): $M_{23}C_6$, $MoNi_3$, $M_6C$, MX, MX (−2% unit cell edges), $M_2X$. The authors search on four d-values computed from reciprocal lattice distances forming the sides and diagonals of a parallelogram. This data is redundant, and was reduced to the two largest d-values and included angle (as described above) for the search with ZONES.

Two patterns indexed as $M_2X$, were searched with M=Cr, Ni, Fe, Mo, Nb. These yielded hits, $Nb_2C$ (the same two database entries), for each pattern in Tables 10 and 11. None of the other four metals, singly or in combination, yielded hits for these patterns. In the full practice of this invention, the element Nb would have been determined experimentally, and other combinations of possible metals would be unnecessary to search. In this example three other phases were found to match one but not both patterns, demonstrating the advantage of obtaining alternate orientation patterns for confirmation.

When Ni was used as the metal in the search, three database entries for $Ni(OH)_2$ were found for each pattern (Tables 12, 13). Though not mentioned by the authors of Reference 14, this ought to be considered as an additional possible solution. This $MX_2$ formula was not among those considered by the authors, however. A third low index zone axis pattern was indexed by the authors as an $M_6C$ phase. The best matches from our database were $Cr_3Nb_3C$ (Table 14), and $Fe_3Nb_3C$ and $Fe_3Nb_3$ (Table 15). All possible combinations of one or two metals, M, were searched.

Example 8

A $ZrH_2$ pattern was indexed in Reference 15. Taken as an unknown containing Zr, we obtained two correct hits from the database, both $ZrH_2$, which are listed in Table 16.

Example 9

Table 17 contains results of simulated ZONES searches for 10 phases, representing all crystal systems, in which input of the maximum $d_1$/maximum $d_2$ and the minimum $d_1$/minimum $d_2$ zones for the input phase in the database are, respectively, matched against the entire database. Although all input phases were minerals, this fact was not used in the search. The total number of "Hits" and the number of "Correct" hits are listed in each case (Hits/Corr.). Typical common phases like these have multiple database entries from different experimental sources, each having its own CODE. The large percentage of virtually identical correct hits in each case demonstrates that this search/match scheme is very robust. Many incorrect solutions were closely related solid solutions or isomorphs. Examples of these are: for halite—Na(Cl, CN); for pyrite—FeS and $Fe_2S_3$; for calcite—$CaC_2B_2$.

By way of comparison to the patented procedure mentioned above (Reference 9), the reduced unit cell of each phase (represented by its CODE) in Table 17 was searched against the database, and the total number of hits and correct hits (Hits/Corr. Red. Cell) were entered in the last column of Table 17. Generally similar results were obtained by both search methods, except in crystallographically less well defined cases (albite, kaolinite, and to a lesser extent quartz) where our approach produced more hits. Structurally similar phases with different unit cells (especially crystal symmetry) will not always be found in the reduced unit cell search of the NIST procedure Since d-values are more closely related to structure than unit cells and are often nearly equal among polymorphs and isomorphs, ZONES does tend to produce more hits. Also, as discussed above, reduced unit cells can be difficult to obtain by electron diffraction.

The present invention allows the use of the reduced unit cell parameters instead of the more common procedure of using the full symmetry unit cell, and results in calculating d-spacings produced by double diffraction in addition to those produced by normal diffraction. Also, no d-spacings possible to be calculated from an experimental electron diffraction pattern are missing from among the calculated d-spacings in the database, and no extra d-spacings are present in the database that are not possible to be observed in electron diffraction.

Because of the above, the candidate material or materials found in the output table tblZones2 described above, by using the methods and procedures of this invention, are very likely to be the actual material or materials in the sample from which the electron diffraction pattern was obtained. Additionally, the known materials which are in the database but which are not in the final list of candidate materials are very unlikely to be the actual material or materials in the sample from which the electron diffraction pattern was obtained.

The invention also provides a reduction in the time required to interpret a single crystal electron diffraction pattern of spots from that required by other methods and procedures.

This invention also allows transmission electron microscopists who are not trained crystallographers to identify small single crystal samples of known materials in the database, without resorting to other techniques or references, and in a time period which is comparable to that required by experts skilled in crystallography who employ methods and procedures of this invention or other methods and procedures. While skills in crystallography and database management are required to construct a useful embodiment of this invention, no such skills are required to use such a useful embodiment to identify an unknown single crystal, given the experimental data.

Also, the invention allows individuals who are not skilled in the art of transmission electron microscopy to interpret single crystal electron diffraction patterns obtained by other individuals who are skilled in the art of transmission electron microscopy. As shown in Examples 4–8, in which experimental data obtained by others and reported in the open literature was successfully interpreted by the inventor, who is not skilled in the art of transmission electron microscopy, using the methods and procedures of this invention, without resorting to other references or other methods and procedures.

As a result of the present invention the field of electron diffraction is made more useful to individuals who are not skilled in all three of the following arts: transmission electron microscopy, crystallography, and computer programming, and to the very few who are skilled in all three arts.

Illustrative examples of suitable method for the identification of polycrystalline materials from electron diffraction patterns, relevant crystallographic theory and application, and the techniques of electron diffraction can be found in the following literature and the description thereof are herein incorporated by reference:

1. Andrews, K. W., Dyson, D. J., and Keown, S. R., Interpretation of Electron Diffraction Patterns, Second Edition, Adam Hilger, London, 1971, p. 15.
2. Lally, J. S. and Lee, R. J., Computer Indexing of Electron Diffraction Patterns Including the Effect of Lattice Symmetry, Proc. Electron Microsc. Soc. Am., 1977, pp. 22–23.
3. Lally, J. S. and Lee, R. J., Computer Indexing of Electron Diffraction Patterns Including the Effect of Lattice Symmetry, Electron Microsc. X-ray Appl. Envirn. Occup. Health Anal., Second Symposium, Phillip A. Russell., Alan E. Hutchings, eds., Ann Arbor Sci., Ann Arbor, Mich., 1978, pp. 169–174.

4. Kasper, John S. and Lonsdale Kathleen, eds. (1972), International Tables for X-ray Crystallography, V. II, 3rd ed., Knoch Press, Birmingham, U.K., 106.
5. Mighell, Alan, and Karen, Vicky Lynn (1996), NIST Crystallographic Databases for Research and Analysis, Journal of Research of the National Institute of Standards and Technology, v. 101, No. 3, 273–280.
6. Anderson, Ron, Mighell, Alan D., Karen, Vicky Lynn, Jenkins, Ron, and Carr, Martin J. (1993), Electron Diffraction Databases, Microscopy Society of America Bulletin, v. 23, No. 1, 128–137.
7. Mighell, A. D., Himes, V. L., Anderson, R., and Carr, M. J. (1988), D-spacing/Formula Index for Compound Identification using Electron Diffraction Data, Proc. Ann. Meeting Electron Miscros. Soc. Am., 46th, 912–913.
8. Stalick, Judith K., and Mighell, Alan D. (1986), Crystal Data, Version 1.0 Database Specifications, NBS Technical Note 1229, National Bureau of Standards.
9. Karen, V. L. and Mighell, A. D., U.S. Pat. Nos. 5,168,457 (1992), Apparatus for Identifying and Comparing Lattice Structures and Determining Lattice Structure Symmetries; and 5,235,523 (1993), Apparatus and Methods for Identifying and Comparing Lattice Structures and Determining Lattice Structure Symmetries.
10. Booth, M., Gittos, M., and Wilkes, P., A General Program for Interpreting Electron Diffraction Data, Metallurgical Transactions, Vol. 5, March 1974, pp. 775–776.
11. Wilkes, P., Complete Indexing of Electron Diffraction Patterns by Computer, Journal of Materials Science, 9, 1974, pp. 517–518.
12. Goehner, Raymond P., Prakask, Rao, Computer-aided Indexing of Transmission Electron Diffraction Patterns, Metallography, 10, 1977, pp. 415–424.
13. Dimov, V., Iamakov, V., and Bozhilov, K., Automated Identification of Monocrystal Microphases in Transmission Electron Microscopy (TEM), Computers & Geosciences, Vol. 20, No. 9, pp. 1267–1273.
14. Griem, Walter, Schwaab, Paul, Computer Assisted Indexing of Electron Diffraction Patterns (article in German and English), Praktische Metallographie, 14, 1977, pp. 389–409.
15. Ploc, R. A., At. Energy Can. Ltd., [Rep.] AECL (1976), AECL-5556, p. 50.

TABLE 1

Stored Zones

| Zone Number | U, V, W | $D_1$<br>$H_1, k_1, l_1$ | $d_2$<br>$h_2, k_2, l_2$ |
|---|---|---|---|
| 1 | 0, 0, 1 | 1, 0, 0 | 0, 1, 0 |
| 2 | 0, 1, 0 | 1, 0, 0 | 0, 0, 1 |
| 3 | 1, 0, 0 | 0, 1, 0 | 0, 0, 1 |
| 4 | 0, 1, -1 | 1, 0, 0 | 0, 1, 1 |
| 5 | 1, 0, -1 | 0, 1, 0 | 1, 0, 1 |
| 6 | 1, -1, 0 | 0, 0, 1 | 1, 1, 0 |
| 7 | 0, 1, 1 | 1, 0, 0 | 0, 1, -1 |
| 8 | 1, 0, 1 | 0, 1, 0 | 1, 0, -1 |
| 9 | 1, 1, 0 | 0, 0, 1 | 1, -1, 0 |
| 10 | -1, 1, 1 | 1, 1, 0 | 1, 0, 1 |
| 11 | 1, -1, 1 | 1, 1, 0 | 0, 1, 1 |
| 12 | 1, 1, -1 | 1, 0, 1 | 0, 1, 1 |
| 13 | -1, 1, 2 | 1, 1, 0 | 1, -1, 1 |
| 14 | 1, -1, 2 | 1, 1, 0 | 1, -1, -1 |
| 15 | -1, 2, 1 | 1, 0, 1 | 1, 1, -1 |
| 16 | 1, 2, -1 | 1, 0, 1 | 1, -1, -1 |
| 17 | 2, 1, -1 | 0, 1, 1 | 1, -1, 1 |
| 18 | 2, -1, 1 | 0, 1, 1 | 1, 1, -1 |
| 19 | 1, 1, 1 | 1, -1, 0 | 1, 0, -1 |
| 20 | 1, 1, -2 | 1, -1, 0 | 1, 1, 1 |

TABLE 1-continued

Stored Zones

| Zone Number | U, V, W | $D_1$<br>$H_1, k_1, l_1$ | $d_2$<br>$h_2, k_2, l_2$ |
|---|---|---|---|
| 21 | 1, 1, 2 | 1, -1, 0 | 1, 1, -1 |
| 22 | 1, -2, 1 | 1, 0, -1 | 1, 1, 1 |
| 23 | 1, 2, 1 | 1, 0, -1 | 1, -1, 1 |
| 24 | -2, 1, 1 | 0, 1, -1 | 1, 1, 1 |
| 25 | 2, 1, 1 | 0, 1, -1 | 1, -1, -1 |

TABLE 2

Fluorite (CaF$_2$). $d_1$ = 3.19, $d_2$ = 3.18, $\phi$ =70.2 deg. Err. d = 1.5%, err. = 1 deg. Element: Ca.

| CODE | Formula | $d_1$ (largest) | $d_2$ | $\phi$ |
|---|---|---|---|---|
| 022526 | CaF2 | 3.15 | 3.15 | 70.5 |
| 037401 | Ca | 3.22 | 3.22 | 70.5 |
| 121858 | CaF2 | 3.15 | 3.15 | 70.5 |
| 713957 | CaF2 | 3.15 | 3.15 | 70.5 |
| F901289 | CaF2 | 3.15 | 3.15 | 70.5 |
| F902585 | CaF2 | 3.15 | 3.15 | 70.5 |

TABLE 3

Zircon (ZrSiO$_4$). $d_1$ = 4.51, $d_2$ = 2.69, $\phi$ =78.6. Err. d = 1.5%, err. $\phi$ = 1.0 deg. elements: Zr, Si.

| CODE | Formula | $d_1$ (largest) | $d_2$ | $\phi$ |
|---|---|---|---|---|
| 026003 | ZrSiO4 | 4.45 | 2.65 | 77.7 |
| 803775 | ZrSiO4 | 4.44 | 2.65 | 77.8 |
| F902440 | ZrSiO4 | 4.44 | 2.65 | 77.9 |

TABLE 4

Molybdite(MoO$_3$), common zone: $d_1$ = 3.96, $d_2$ = 3.70, $\phi$ = 90.0. Err. d = 1.5%, err. $\phi$ = deg. Element: Mo.

| CODE | Formula | $d_1$(largest) | $d_2$ | $\phi$ |
|---|---|---|---|---|
| 003676 | MoO3 | 3.96 | 3.69 | 90 |
| 023201 | MoO3 | 3.93 | 3.67 | 90 |
| 027566 | MoO3 | 3.95 | 3.69 | 90 |
| 713757 | MoO3 | 3.96 | 3.69 | 90 |
| F902107 | MoO3 | 3.96 | 3.69 | 90 |
| F941944 | MoO3 | 3.93 | 3.69 | 90 |

TABLE 5

Hornblende, first zone, data from Reference 8. $d_1$ = 18.00, $d_2$ = 9.57, $\phi$ =90.0. Err. d = 1.5%, err = 1.0 deg. Elements: Ca, Fe, Mg, Si.

| CODE | Formula | $d_1$(largest) | $d_2$ | $\phi$ |
|---|---|---|---|---|
| 036656 | Ca2(Mg, Fe)5Si8O22(OH, F)2 | 18.06 | 9.50 | 90 |
| 036659 | Ca2(Mg, Fe)5Si8O22(OH, F)2 | 18.09 | 9.49 | 90 |
| 036667 | Ca2(Fe, Mg)5Si8O22(OH, F)2 | 18.13 | 9.53 | 90 |
| 036670 | Ca2(Mg, Fe)5Si8O22(OH, F)2 | 18.10 | 9.53 | 90 |
| 036671 | Ca2(Mg, Fe)5Si8O22(OH, F)2 | 18.08 | 9.49 | 90 |
| 109098 | Ca3Fe(Mg, Fe)4Si8O22(OH)2 | 18.12 | 9.52 | 90 |

TABLE 6

Hornblende, second zone, data from Reference 9. $d_1 = 8.47$, $d_2 = 5.15$, $\phi = 76.8$. Err. d = 1.5%, err. $\phi$ 1.0 deg.

| CODE | Formula | $d_1$ (largest) | d2 | $\phi$ |
|---|---|---|---|---|
| 036656 | Ca2(Mg, Fe)5Si8O22(OH, F)2 | 8.41 | 5.13 | 76 |
| 036659 | Ca2(Mg, Fe)5Si8O22(OH, F)2 | 8.41 | 5.12 | 76 |
| 036667 | Ca2(Fe, Mg)5Si8O22(OH, F)2 | 8.43 | 5.15 | 76 |
| 036670 | Ca2(Fe, Mg)5Si8O22(OH, F)2 | 8.43 | 5.11 | 75 |
| 036670 | Ca2(Fe, Mg)5Si8O22(OH, F)2 | 8.43 | 5.14 | 76 |
| 036671 | Ca2(Mg, Fe)5Si8O22(OH, F)2 | 8.40 | 5.12 | 76 |
| 037155 | Ca2(Mg, Fe)5Si8O22(OH)2 | 8.44 | 5.12 | 77 |
| 109098 | Ca3Fe(Mg, Fe)4Si8O22(OH)2 | 8.43 | 5.10 | 76 |
| 109098 | Ca3Fe(Mg, Fe)4Si8O22(OH)2 | 8.43 | 5.11 | 76 |
| E721167 | Ca2(Mg, Fe)5Si8O22(OH)2 | 8.41 | 5.11 | 77 |
| E721167 | Ca2(Mg, Fe)5Si8O22(OH)2 | 8.42 | 5.11 | 77 |
| F900783 | Ca2(Mg, Fe)5Si8O22(OH)2 | 8.46 | 5.12 | 77 |

TABLE 7

Fe3C, data from Reference 10. $d_1 = 5.16$, $d_2 = 4.66$, $\phi = 90$. Err. d = 4%, err. $\phi$ =2 deg. Elements: Fe.

| CODE | Formula | $d_1$(largest) | $d_2$ | $\phi$ |
|---|---|---|---|---|
| 038237 | Fe3C | 5.07 | 4.52 | 90 |
| 038290 | Fe3C | 5.08 | 4.52 | 90 |
| 038291 | Fe3C | 5.08 | 4.52 | 90 |
| 038308 | Fe3(C, B) | 5.27 | 4.48 | 90 |
| 712191 | Fe3C | 5.09 | 4.52 | 90 |
| 713913 | Fe3C | 5.09 | 4.52 | 90 |

TABLE 8

Hollandite, BaMn8O16, data from Reference 11. First zone: $d_1 = 5.000$, $d_2 = 2.7500$, $\phi = 88.75$. Err. d = 1.5%, err. $\phi$ = 1.0 deg. Elements: Ba, Mn.

| CODE | Formula | $d_1$(largest) | $d_2$ | $\phi$ |
|---|---|---|---|---|
| 712343 | BaMn8O16 | 5.01 | 2.75 | 89.7 |
| 712343 | BaMn8O16 | 5.01 | 2.75 | 89.8 |
| B716966 | BaMn8O16 | 5.01 | 2.75 | 89.7 |
| B716966 | BaMn8O16 | 5.01 | 2.75 | 89.8 |
| F901805 | BaMn8O16 | 5.00 | 2.74 | 89.7 |

TABLE 9

Hollandite, second zone: $d_1 = 7.150$, $d_2 = 2.764$, $\phi = 79.00$. Err. d = 1.5%, err. $\phi$ = 1.0 deg.

| CODE | Formula | $d_1$(largest) | $d_2$ | $\phi$ |
|---|---|---|---|---|
| 712343 | BaMn8O16 | 7.04 | 2.76 | 79.0 |
| 712343 | BaMn8O16 | 7.04 | 2.76 | 79.1 |
| B716966 | BaMn8O16 | 7.04 | 2.76 | 79.0 |
| B716966 | BaMn8O16 | 7.04 | 2.76 | 79.1 |
| F901805 | BaMn8O16 | 7.04 | 2.75 | 79.0 |
| F901805 | BaMn8O16 | 7.04 | 2.75 | 79.1 |

TABLE 10

$M_2X$, data from Reference 12, first zone: $d_1 = 2.74$, $d_2 = 2.74$, $\phi = 60.0$. Err. d = 2%, err. $\phi$ = 1 deg. Element: Nb.

| CODE | Formula | $d_1$(largest) | $d_2$ | $\phi$ |
|---|---|---|---|---|
| 020498 | NbFO2 | 2.76 | 2.76 | 60.0 |
| 024797 | NbF3 | 2.76 | 2.76 | 60.0 |
| 029083 | NbFO2 | 2.75 | 2.75 | 60.0 |

TABLE 10-continued $M_2X$, data from Reference 12, first zone: $d_1 = 2.74$, $d_2 = 2.74$, $\phi = 60.0$. Err. d = 2%, err. = 1 deg. Element: Nb.

| CODE | Formula | $d_1$(largest) | $d_2$ | $\phi$ |
|---|---|---|---|---|
| 020498 | NbFO2 | 2.76 | 2.76 | 60.0 |
| 033009 | NbFO2 | 2.76 | 2.76 | 60.0 |
| 037977 | Nb2C | 2.69 | 2.69 | 60.0 |
| 108416 | Nb2C | 2.69 | 2.69 | 60.0 |
| 120058 | Nb4C3 | 2.71 | 2.71 | 60.8 |
| 713883 | NbB2 | 2.69 | 2.69 | 60.0 |

TABLE 11

$M_2X$, second zone: $d_1 = 2.74$, $d_2 = 1.47$, $\phi = 90.0$. Err. d = 2%, err. $\phi$ = 1 deg. Element: Nb.

| CODE | Formula | $d_1$(largest) | $d_2$ | $\phi$ |
|---|---|---|---|---|
| 025091 | NbN | 2.77 | 1.48 | 90.0 |
| 037977 | Nb2C | 2.69 | 1.48 | 90.0 |
| 108416 | Nb2C | 2.69 | 1.48 | 90.0 |

TABLE 12

$M_2X$, first zone. Err. d = 2%, err. $\phi$ = 1 deg. Element: Ni.

| CODE | Formula | $d_1$(largest) | $d_2$ | $\phi$ |
|---|---|---|---|---|
| 026059 | Ni(OH)2 | 2.71 | 2.71 | 60.0 |
| 109600 | Ni2NO3(OH)3 | 2.71 | 2.71 | 60.0 |
| 700438 | Ni3(NO3)2(OH)4 | 2.71 | 2.71 | 60.0 |
| 809675 | Ni(OH)2 | 2.71 | 2.71 | 60.0 |

TABLE 13

$M_2X$, second zone. Err. d = 2%, err. $\phi$ =1 deg. Element: Ni.

| CODE | Formula | $d_1$(largest) | $d_2$ | $\phi$ |
|---|---|---|---|---|
| 020986 | Ni(OH)2 | 2.7 | 1.48 | 90.0 |
| 026059 | Ni(OH)2 | 2.71 | 1.48 | 90.0 |
| 809675 | Ni(OH)2 | 2.71 | 1.48 | 90.0 |

TABLE 14

$M_6C$. $d_1 = 6.35$, $d_2 = 3.94$, $\phi = 90.0$. Err. d = 5%, err. $\phi$ = 1 deg. Elements: Cr, Nb.

| CODE | Formula | $d_1$(largest) | $d_2$ | $\phi$ |
|---|---|---|---|---|
| 037846 | Cr3Nb3C | 6.63 | 4.06 | 90. |

TABLE 15

$M_6C$. Err. d = 3%, err. $\phi$ = 1 deg. Elements: Fe, Nb.

| CODE | Formula | $d_1$(largest) | $d_2$ | $\phi$ |
|---|---|---|---|---|
| F722506 | Fe3Nb3C | 6.52 | 3.99 | 90.0 |
| G726169 | Fe21.988(Nb0.167B0.833)6 | 6.24 | 3.82 | 90.0 |

TABLE 15-continued $M_6C$. Err. d = 3%, err. φ = 1 deg. Elements: Fe, Nb.

| CODE | Formula | $d_1$(largest) | $d_2$ | φ | 0 |
|---|---|---|---|---|---|
| H727408 | B18Fe76Nb6 | 6.25 | 3.82 | 90.0 | |

TABLE 16

$ZrH_2$, data from Reference 13. $d_1$ = 4.912, $d_2$ = 3.367, φ = 90.0. Err. d = 2%, err. φ =1.0 deg. Element: Zr.

| CODE | Formula | $d_1$(largest) | $d_2$ | φ | 027550 |
|---|---|---|---|---|---|
| 102483 | ZrH2 | 4.99 | 3.32 | 90.0 | |

TABLE 17

Search Simulations. CS = crystal system:
A = anorthic(triclinic), M = monoclinic, O = orthorhombic, T = tetragonal,
R = rhombohedral, H = hexagonal, C = cubic. First Entry for each phase
is maximum $d_1$, $d_2$. Second entry is minimum $d_1$, $d_2$. Error limits:
1.5%, 1 deg.

| CODE | Name | Formula | CS | d1 | d2 | phi | Hits/Corr. | Hits/Corr. Red. Cell |
|---|---|---|---|---|---|---|---|---|
| 000449 | Albite | Na(Si3Al)O8 | A | 6.38 | 6.38 | 86.4 | 12/11 | 6/6 |
| | | | | 4.02 | 3.78 | 70.6 | 13/13 | |
| 038274 | Aragonite | CaCO3 | 0 | 7.96 | 5.73 | 90.0 | 7/6 | 6/6 |
| | | | | 3.75 | 3.39 | 82.4 | 6/6 | |
| 038065 | Calcite | CaCO3 | R | 5.68 | 4.19 | 75.8 | 9/9 | 7/7 |
| | | | | 2.68 | 2.49 | 90.0 | 10/7 | |
| 003505 | Gypsum | CaSO4!2H2O | M | 7.58 | 5.37 | 69.3 | 7/7 | 7/7 |
| | | | | 3.55 | 3.17 | 86.0 | 7/7 | |
| 033122 | Halite | NaCl | C | 3.25 | 3.25 | 70.5 | 3/3 | 3/3 |
| | | | | 1.99 | 1.70 | 90.0 | 4/3 | |
| 001144 | Kaolinite | Al2(OH)4Si2O5 | A | 8.95 | 7.14 | 88.1 | 2/2 | 1/2 |
| | | | | 4.12 | 3.68 | 72.4 | 6/6 | |
| 003676 | Molybdite | MoO3 | O | 13.9 | 3.96 | 90.0 | 5/5 | 4/4 |
| | | | | 2.70 | 2.65 | 86.0 | 5/5 | |
| 024148 | Pyrite | FeS2 | C | 5.41 | 5.41 | 90.0 | 12/10 | 12/12 |
| | | | | 3.83 | 3.12 | 90.0 | 12/10 | |
| 026970 | Quartz | SiO2 | H | 5.40 | 4.25 | 90.0 | 24/23 | 22/22 |
| | | | | 3.34 | 2.28 | 71.8 | 29/29 | |
| 807069 | Zircon | ZrSiO4 | T | 4.66 | 4.66 | 90.0 | 17/14 | 14/14 |
| | | | | 2.98 | 2.64 | 63.7 | 14/14 | |

It will be apparent from the foregoing that many other variations and modifications may be made regarding the methods described herein, without departing substantially from the essential features and concepts of the present invention. Accordingly, it should be clearly understood that the forms of the invention described herein are exemplary only and are not intended as limitations on the scope of the present invention as defined in the appended claims.

What is claimed is:

1. A method for creating a searchable database of crystal electron diffraction data comprising:
(a) creating tables within a relational database, said tables comprising Code data, Formula data, and Element data; wherein said Code data includes information relating to the d-spacings and acute angles of diffraction patterns of crystals, said Formula data includes information relating to the chemical formulae of said crystals, and said Element data includes information relating to the presence of elements of high atomic number in said crystals;
(b) creating at least one macro for performing searches using said tables; said at least one macro including the steps of:
(i) requesting input data relating to observed d-spacings, acute angles, experimental error limits, and anticipated atomic numbers of an experimental sample;
(ii) comparing said input data with the data in said tables in accordance with said experimental error limits; and
(iii) generating at least one report listing the crystals within said tables that match said input data.

2. The method for creating a searchable database of crystal electron diffraction data according to claim 1, wherein said Code data is derived from reduced unit cell parameters, and said step of comparing said input data includes calculating d-spacings produced by double diffraction.

3. A method for classifying crystal electron diffraction data obtained from an experimental sample, comprising:
(a) generating a relational database comprising:
(i) at least three tables holding Code data, Formula data, and Element data, respectively; wherein said Code data includes information relating to the d-spacings and acute angles of diffraction patterns of crystals, said Formula data includes information relating to the chemical formulae of said crystals, and said Element data includes information relating to the presence of elements of high atomic number in said crystals;
(ii) at least one macro for performing searches using said tables; said at least one macro including the steps of:
(1) requesting input data relating to observed d-spacings, acute angles, experimental error limits, and anticipated atomic numbers of an experimental sample;
(2) comparing said input data with the data in said tables in accordance with said experimental error limits; and (3) generating at least one report listing the crystals within said tables that match said input data; and (b) using said macro of said relational database to enter electron diffraction data obtained from said experimental sample and to obtain said at least one report.

4. The method for classifying crystal electron diffraction data according to claim 3, wherein said Code data is derived from reduced unit cell parameters, and said step of comparing said input data includes calculating d-spacings produced by double diffraction.

5. A relational database for classifying crystal electron diffraction data obtained from an experimental sample, said database comprising:

(a) at least three tables holding Code data, Formula data, and Element data, respectively; wherein said Code data includes information relating to the d-spacings and acute angles of diffraction patterns of crystals, said Formula data includes information relating to the chemical formulae of said crystals, and said Element data includes information relating to the presence of elements of high atomic number in said crystals;

(b) at least one macro for performing searches using said tables; said at least one macro including the steps of:

(i) requesting input data relating to observed d-spacings, acute angles, experimental error limits, and anticipated atomic numbers of an experimental sample;

(ii) comparing said input data with the data in said tables in accordance with said experimental error limits; and (iii) generating at least one report listing the crystals within said tables that match said input data.

6. The relational database according to claim 5, wherein said Code data is derived from reduced unit cell parameters, and said step of comparing said input data includes calculating d-spacings produced by double diffraction.

* * * * *